United States Patent
Zhang et al.

(10) Patent No.: US 8,521,446 B2
(45) Date of Patent: Aug. 27, 2013

(54) SYSTEM AND METHOD OF CONDUCTING REFRACTION ANGLE VERIFICATION FOR PHASED ARRAY PROBES USING STANDARD CALIBRATION BLOCKS

(75) Inventors: Jinchi Zhang, Quebec (CA); Jason Habermehl, Quebec (CA)

(73) Assignee: Olympus NDT Inc., Waltham, MA (US)

( * ) Notice: Subject to any disclaimer, the term of this patent is extended or adjusted under 35 U.S.C. 154(b) by 275 days.

(21) Appl. No.: 12/953,252

(22) Filed: Nov. 23, 2010

(65) Prior Publication Data
US 2012/0130653 A1    May 24, 2012

(51) Int. Cl.
*G01B 5/00* (2006.01)
*G10K 11/00* (2006.01)

(52) U.S. Cl.
USPC ............................................ 702/39; 702/103

(58) Field of Classification Search
USPC ............... 702/159, 39, 56, 35, 103, 170, 171; 73/624, 598, 597, 618, 627, 1.82; 367/13
See application file for complete search history.

(56) References Cited

U.S. PATENT DOCUMENTS

| | | | |
|---|---|---|---|
| 7,578,166 B2* | 8/2009 | Ethridge et al. | 73/1.82 |
| 7,891,247 B2* | 2/2011 | Ihn | 73/602 |
| 8,156,784 B2* | 4/2012 | DeAngelo et al. | 73/1.82 |
| 8,171,771 B2* | 5/2012 | Hain et al. | 73/1.82 |
| 8,265,886 B2* | 9/2012 | Bisiaux et al. | 702/39 |
| 2005/0076703 A1* | 4/2005 | Johnson et al. | 73/1.82 |
| 2005/0156364 A1* | 7/2005 | Bisiaux et al. | 266/79 |
| 2007/0000328 A1* | 1/2007 | Buttram | 73/597 |
| 2009/0266165 A1* | 10/2009 | Greenwood | 73/597 |
| 2011/0083512 A1* | 4/2011 | Imbert et al. | 73/622 |

* cited by examiner

*Primary Examiner* — Marc Armand
*Assistant Examiner* — Ricky Ngon
(74) *Attorney, Agent, or Firm* — Ostrolenk Faber LLP

(57) ABSTRACT

Disclosed is an ultrasonic phased array non-destructive inspection system that includes a PA probe, a conventional PA inspection unit and a refraction angle verification unit. The PA inspection unit is employed to emit ultrasonic angle beams into an AWS IIW Block and to receive a set of corresponding echo signals reflected from the calibration block and to provide time-of-flight (TOF) values corresponding to each angle beam. The refraction angle verification unit then provides a true angle for each of the angle beams based on the ultrasonic and geometric characteristics of the block and the measured TOF values. Other calibration blocks such as the DSC and Nayships blocks can also be used for this purpose.

16 Claims, 6 Drawing Sheets

SYSTEM AND METHOD OF CONDUCTING REFRACTION ANGLE VERIFICATION FOR PHASED ARRAY PROBES USING STANDARD CALIBRATION BLOCKS

BACKGROUND

1. Field of the Disclosure

The present invention relates to non-destructive testing and inspection systems (NDT/NDI), particularly to a system operable for and a method of conducting phased array probes refraction angle verification using standard calibration blocks, including IIW blocks.

2. Related Art

Acoustic phased array (also known as "PA") instruments provide effective inspection to detect flaws in many kinds of test objects, such as welded steel structures. It is widely known that PA instruments produce accurate, detailed cross-sectional pictures of internal structures at fast inspection speeds. Phased array technology uses multiple acoustic elements and electronic time delays to create beams that can be steered, scanned, swept, and focused electronically for fast inspection and multiple angle inspections.

A PA system is programmed to steer sound beams in a wedge medium and then, being governed by the Snell law, the sound beams propagate through the wedge-test piece interface to form sound beams at inspection angles in the test piece. These inspection angles are called "refraction angles". Due to the complexity of the procedure, the refraction angles generated by a PA system are usually not verified or checked during existing inspection operations, despite the well-known fact that the Snell law can overestimate the refraction angles at high angles of shear waves, as is illustrated in a publication in the figure 4.29b in Section 4.6 of *Ultrasonic Testing of Materials*, 4$^{th}$ Edition published by Springer-Verlag, 1990.

In existing practice, to conduct a typical angular scan, the user usually relies heavily on the initial values of refraction angles calculated by the focal law calculator integrated in the PA instrument. A very common practice is that, without checking the refraction angles, the user conducts the 'Wedge Delay Calibration' with a reference reflector of known depth or known sound path in a calibration block. This procedure, by simply adjusting the beam delays in wedge, compensates for any discrepancy in the actual measurement of the known depth or known sound path. However, the discrepancy may not be induced by the wedge delays. Instead, it maybe induced by other inaccurate parameters such as the velocity in wedge, velocity in the test material, the geometrical inaccuracy of the wedge or even the inaccuracy in the electronic firing/reception. Consequently, using only the beam delays in wedge to compensate the discrepancy is not completely reliable.

The use of the function 'wedge delay calibration' cannot modify or update the refraction angles, but only provide compensation to correct the displayed depth or sound path to the known depth or known sound path based on the reference flaw. The refraction angle is left without any calibration in this existing practice. If the displayed refraction angle is not what the true refraction angle is, the PA instrument may induce errors elsewhere, such as the horizontally measured distance between the measured flaw and the front of the wedge would be nearer or farther than that of the true values.

In another existing practice, some phased array system users check refraction angles by following a procedure similar to the single element ultrasound (UT) refraction angle check. The procedure is detailed in *ANSI Standard by American Welding Society*, "AWS D1.1/D1.1M: 2006", more particularly in *Calibration of the UT Unit with IIW Block*, in sections 6.29.2 Shear Wave Mode (Transverse) on Index Point and Angle and the associated figures 6.22 and 6.26. The procedure is herein referred as "ANSI Calibration" procedure which is herein incorporated by reference by the present application.

The above cited procedure of refraction angle check is not practical for phased array operation for multiple reasons, some of which are listed as follows.

Due to the involvement of many different beam angles, it is difficult to physically mark the beam exit point for each beam on the side of the PA search unit.

Due to the nature of the manual operation, the accuracy of the angle verification using the above ANSI Calibration is not desirable.

More existing effort in providing PA beam refraction angle check is disclosed by U.S. Pat. No. 6,938,457B2. The principle of the disclosed measurement procedure is guided by the manual ANSI Calibration method described above. The probe index point, according to this patent, still needs to be physically marked and the refraction angle (i.e.: the so-called induced angle in the patent) is measured with a series of scribed angle lines extended from a side-drilled hole.

It is obvious that the above ANSI Calibration operation is time consuming since the user needs to manually write down the angle values and, if necessary, to manually input the values into the PA instrument for further processing.

Thus, given the drawbacks and problems that existing methods of conducting beam angle checks, there is a need to provide a phased array angle beam check method that can be efficiently and conveniently conducted with high accuracy.

SUMMARY

It is a general object of this invention to provide a system and a method to enable conducting verification of phased array beam angles in an efficient manner with high accuracy.

It is a further object of the present invention to provide a software module executable to enable the beam angle verification for a phased array system. The software module can be either connected to or built into a phased array system.

It is a further object of the present invention to provide a computer-assisted process for verification of PA beam refraction angles.

It is a further object of the present invention to provide a system and method that employs the use of a standard IIW type of block to conduct verification of PA beam refraction angles.

It is a further object of the present invention to provide a system and method for verification of PA beam refraction angles that obviates the need to manually write down or marking the beam exit positions on the wedge body used during the procedure.

It is a further object of the present invention to provide a system and method that provides outputs of both beam angles and wedge delays during the process of beam angle verification.

Advantages inherently provided by the herein disclosed PA beam angle verification system and method include being efficient to operate with highly accurate and consistent results.

DETAILED DESCRIPTION OF THE EMBODIMENTS

Figure 1:
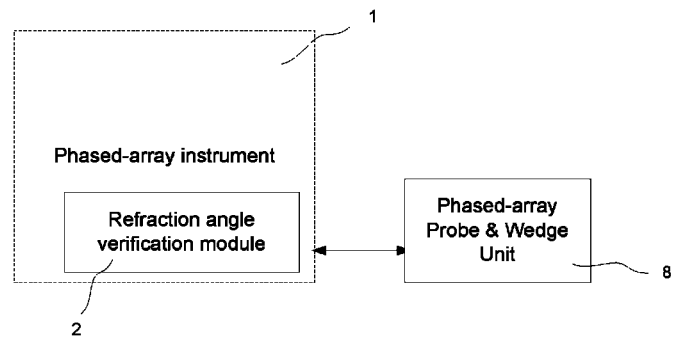
FIG. 1 is a schematic view of the phased array system according to the present invention, wherein a refraction angle verification module is added to a conventional PA system.

Referring to FIG. 1, the phased array system with capability of conducting refraction angle verification comprises a conventional phased array system 1, a refraction angle verification module 2 and a conventional phased array probe and wedge unit 8. Angle verification module 2 can be built-in directly onto a phased array system at development stage, or can be a later add-on to an otherwise existing phased array system 1. With module 2 deployed, PA system 1 can be used to verify the refraction angles of probe 8 conveniently with high accuracy.

PA angle refraction verification module 2 is preferably deployed by loading executable software onto a processor or equivalent logic processor in other programmable devices (e.g., an ASIC or FPGA chip), installed on the PA system 1. The executable software is designed, according to the present disclosure to execute a refraction angle verification process and method described as follows, associated with FIGS. 2 through 6.

Figure 2:
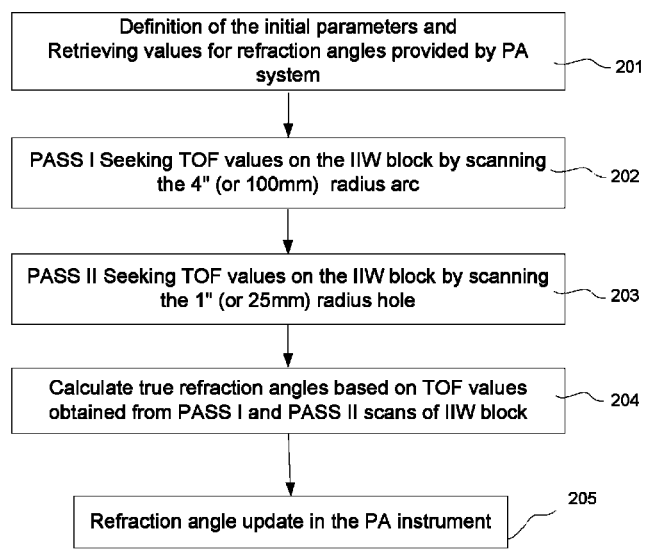
FIG. 2 is a flow-chart depicting the method and process according to the present invention to perform refraction angle verification.

According to FIG. 2, the refraction angle verification can be achieved by verifying beam angles of PA system 1 using an IIW block as shown in the aforementioned reference "ANSI Calibration". The verification process includes steps 201 through 205.

Steps 201 to 203 require the user's interactions and steps 204 and 205 are executed automatically by verification module 2.

Figure 4A:
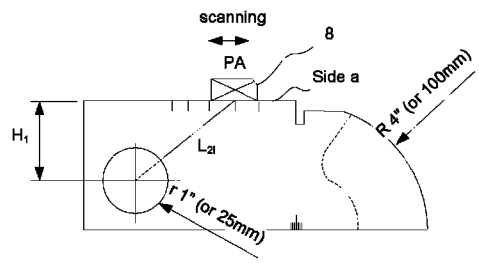
FIGS. 4a and 4b illustrate the geometric parameters associated with a standard IIW block used in the calculation of the true beam angles.
Figure 4B:
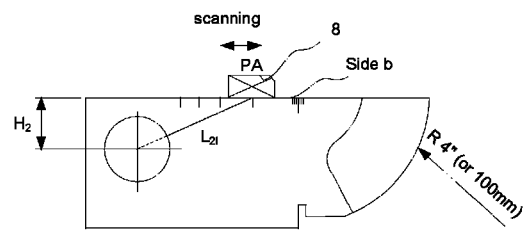

Continuing with FIG. 2, in step 201, the user provides input to PA system 1 for the parameters shown in FIGS. 4a and 4b. The definitions of the geometric parameters based on the usage of the IIW block are given below.

R, the arcuate surface radius of the IIW block (normally 4" or 100 mm).

r, the radius of the largest round hole in the IIW block, normally 1" or 25 mm. It should be noted that there are more than one round holes on a typical IIW block. But only the largest hole of the block is shown on FIGS. 4a, 4b, 6a and 6b.

$H_1$, the depth of the center of the largest hole, measured from the side a where marked angles 35° to 65° are located.

$H_2$, the depth of the center of the largest hole, measured from the side b where marked angles 60° to 75° are located.

The "range of the refraction angles" for verification. For a sectorial scan, the range of refraction angles can be part or the full range of the refraction angles of a specific probe/wedge unit. For a linear scan, the range of refraction angles is a specific refraction angle. It should be noted that the angles for verification should be within range of 35° to 75°, which is typical angle range for IIW blocks if the arcuate surface and the largest round hole are used.

The sound wave velocity V of the IIW block. The refraction angle check procedure of the present disclosure requires beforehand knowledge of the sound wave velocity in the IIW block. Any IIW block that allows a time base distance calibration is suitable for measurement of the wave velocity. One example of such an IIW block is the IIW type US-2 reference block described in Nondestructive Testing Handbook, $2^{nd}$ edition, Vol. 7, page 448~451, published by *American Society for Nondestructive Testing* (ISBN 0-931403-04-09), the content of which is herein incorporated by reference. Preferably, such a modified IIW block is used for the refraction angle verification according to the present disclosure. Otherwise, the wave velocity in the IIW block should be known beforehand.

It should be noted that, at step 201, before each session of refraction angle verification, system 1 already has a set of initial refraction angle values $A_{0i}$, obtained either from a refraction angle calculator provided by most of conventional PA systems, or from the last session of refraction angle verification.

Figure 5:
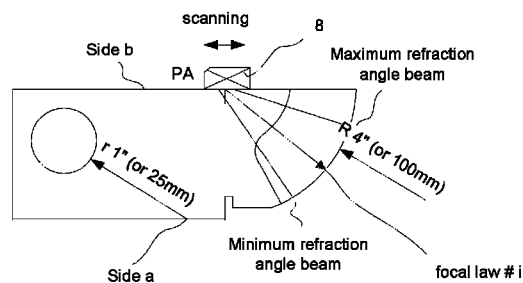
FIG. 5 illustrates the scenario related to Pass I scan obtaining TOF of each sound beam from the beam exit point to the arcuate surface of the IIW block.

Continuing with FIG. 2, in step 202 which is also referred to as "Scan Pass I", the user passes PA probe and wedge unit 8 across through the center of the 4" (or 100 mm) radius of the arcuate surface of the IIW block (see FIG. 5), applying focal laws in a range between the minimum and the maximum refraction angle as shown in FIG. 5.

During the process, the amplitude responses of echo signals are shown on an A-scan for a specific focal law. A gate familiar to those skilled in the art is used for the purpose of choosing only those echo signals reflected from the arcuate (or only from the largest hole for Pass II shown later). For each specific focal law, when the probe unit 8 is moved on side b to scan the actuate surface (see FIG. 5), the maximum amplitude on the A-scan only occurs when the center of probe unit 8 is aligned with the center of the arcuate (the center of the largest hole when in the case of Pass II shown later). Refraction angle verification module 2 instructs PA system 1 to record readings, for each focal law, of the full Time of Flight (later as "TOF") associated with the maximum amplitude response (a peak) measured on the A-scan signal. The full TOF readings across the full focal law range is recorded by the PA system 1 as:

$t_{1i}$ (i=1, 2, . . . to the maximum focal law number), where, i stands for the i number of focal law, "1" in "$t_{1i}$" stands for scan-pass I.

Scan pass II, shown as Step 203 of FIG. 2 is employed to obtain full TOF reading of the 1" (or 25 mm) radius hole (see FIG. 6) when a range of focal laws is applied.

Figure 3:
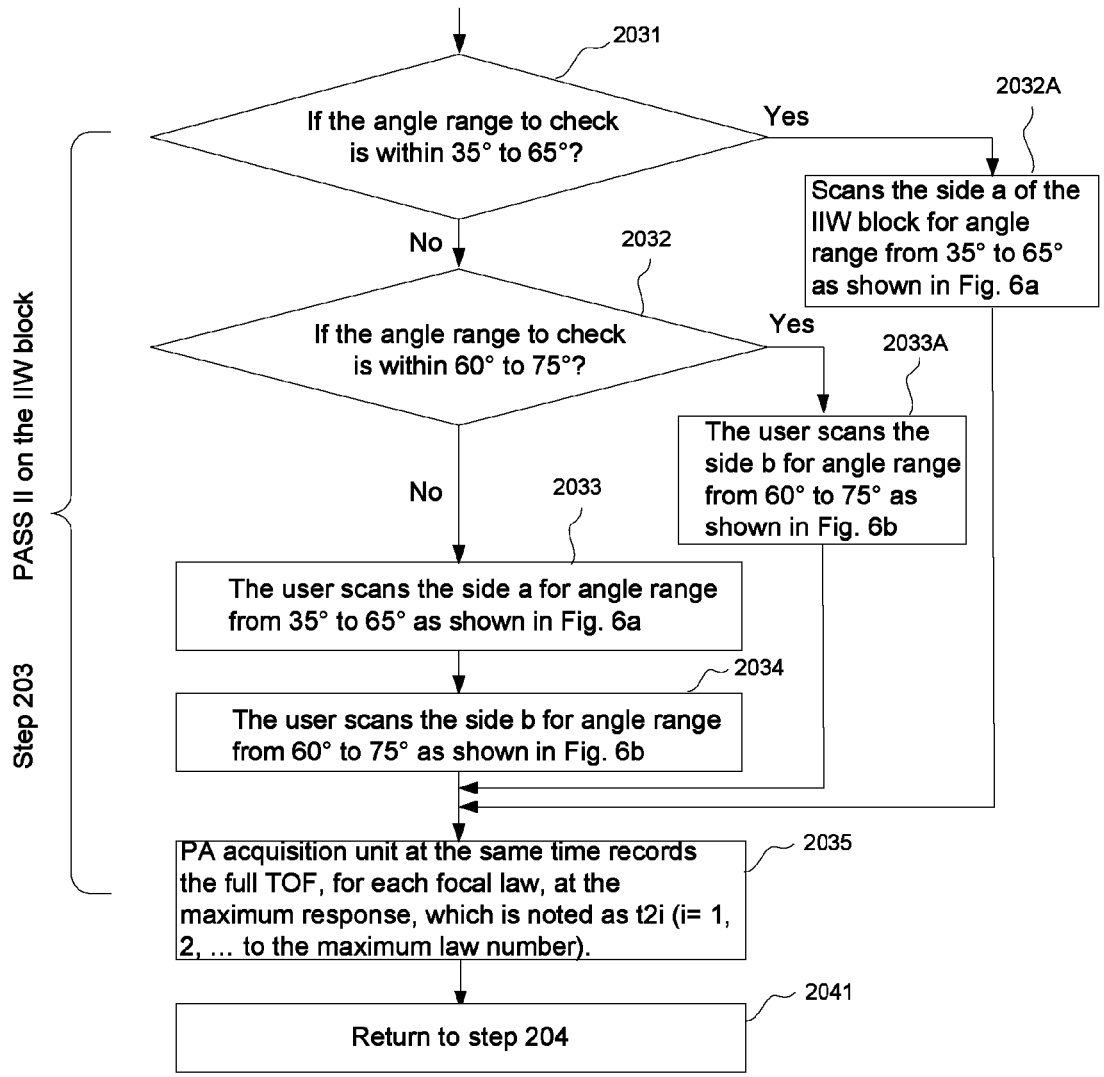
FIG. 3 is a flowchart detailing some of the steps in FIG. 2 (Steps 203 and 204).
Figure 6A:
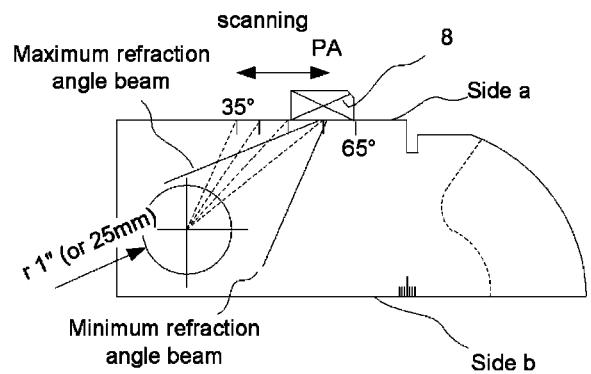
FIGS. 6a and 6b illustrate the scenario related to Pass II scan obtaining TOF of each sound beam from the beam exit point to the round hole of the IIW block.
Figure 6B:
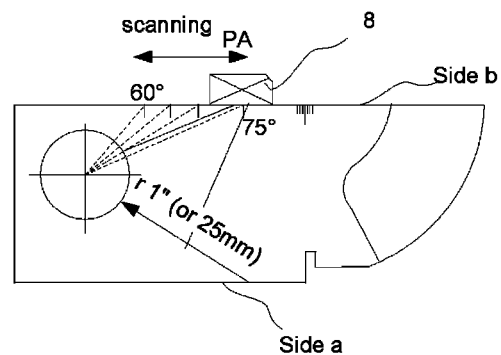

Referring now collectively to FIG. 3 and FIGS. 6a and 6b, which describe a detailed break-down of step 203, in step 2031, angle verification module determines if the angle range to check is within 35° to 65° according to the "range of angle verification" given as the initial input by the operator. If it is yes, then in step 2032A, the user is prompted to scan on side a of the IIW block for angle range from 35° to 65° as shown in FIG. 6a (block 2032A). This scan process is similar to that described above for Pass I in step 202, during which refraction angle verification module 2 instructs PA system 1 to record readings of the TOF for each focal law associated with a maximum amplitude response (a peak) measured.

If it is determined that the angle range to check is not within 35° to 65°, according to the user's input, then in step 2032 refraction angle verification module 2 checks if the refraction angle range for verification is within 60° to 75°, according to the user's input. If yes, then in step 2033A, the user scans on side b for angle range from 60° to 75° as shown in FIG. 6b. If it is not, meaning the angle range for verification includes angles lower than 60° and higher than 65°, the user needs to scan on both side a and side b in steps 2033 and 2034. Similar to Pass I in step 202, during the scan process of both steps 2033 and 2034, angle verification module 2 instructs PA system 1 to record readings of the TOF, for each focal law associated with the maximum amplitude response (a peak) measured.

In step 2035, the angle verification module 2 records the full TOF for each focal law associated with the maximum response recorded in steps 2032A, 2033A, 2033 and 2034, the recorded TOF values for the above scans (herein collectively referred as Pass II) are noted as:

$t_{2i}$ (i=1, 2, . . . to the maximum law number), where, i stands for the i number of focal law, "2" in "$t_{2i}$" stands for scan pass II.

Upon completion of scan pass II at step 2035, the angle rectification process is returned back to step 204 in FIG. 2.

Reference is now turned back to FIG. 2, in the block 204, the angle verification module calculates the above recorded data $t_{1i}$ and $t_{2i}$ using the known parameters provided in step 201.

The following values are to be calculated:

$T_{const}$ is the full TOF from the center of the radius R to the arcuate surface (4" or 100 mm in FIG. 4) and can be calculated using, $$T_{const} = 2 \times R/V. \quad \text{Eq. 1}$$

$T_{const}$ is therefore a constant value for all angle beams.
Full TOF delay in wedge for each law:

$$T_{0i} = t_{1i} - T_{const} \,(i=1, 2, \ldots \text{ to the maximum law number}). \quad \text{Eq. 2}$$

TOF measured from the PA beam exit point to the 1" (or 25 mm) radius hole surface for each law:

$$T_{2i} = t_{2i} - T_{0i} \,(i=1, 2, \ldots \text{ to the maximum law number}). \quad \text{Eq. 3}$$

The sound path from the PA beam exit point to the 1" (or 25 mm) radius hole surface for each law:

$$L_{2i} = T_{2i} \times V/2 \,(i=1, 2, \ldots \text{ to the maximum law number}). \quad \text{Eq. 4}$$

Finally the beam refracting angle in the IIW block for each law is hence deduced as:

$$A_i = \arccos\left(\frac{H_1}{r+L_{2i}}\right) (PA \text{ on side } a), \quad \text{Eq. 5a}$$

or, $$A_i = \arccos\left(\frac{H_2}{r+L_{2i}}\right) (PA \text{ on side } b), \quad \text{Eq. 5b}$$

where $A_i$ represents the results of the calculated beam refraction angles, wherein i represents each focal law number, 1, 2, . . . , to the maximum focal law number.

Then in step 205, the angle verification module 2 updates the system-assumed refraction angles with all the newly calculated refraction angles $A_i$. The PA system now is provided with accurately calibrated refraction angles.

It should be noted and appreciated that other algorithms can also be deployed to determine the refraction angles. They are all within the scope of the present disclosure and should be appreciated by those skilled in the art.

One exemplary variation is to deploy a step of "check box" to see if the initial system value for a refraction angle ($A_{0i}$) is within a predetermined error range comparing to the corresponding measured $A_i$ value. If yes, the angle verification module 2 goes on to calculate the next true refraction angle $A_{o+1}$. Otherwise, angle verification module 2 updates the PA system 1 with the newly calculated refraction angle values $A_i$ before proceeding to calculate $A_{i+1}$.

In another variation, verification module 2 calculates the maximum difference between each measured refraction angle and its corresponding initial refraction angles, as max$|A_i - A_{0i}|$, i=1, 2, . . . , the maximum focal law number. Then verification module 2 compares max$|A_i - A_{0i}|$ with a predetermined error range. If that value is within a predetermined error range, the verification module 2 does not update the refraction angles for the calibration session. Otherwise, verification module 2 updates the PA system 1 with all the newly calculated refraction angle values $A_i$.

The following design variations of the preferred embodiment should be recognized by those skilled in the art to be within the scope of the present disclosure. The detailed description of the following alternative embodiments focuses on the portion of the embodiments that differ from the preferred embodiment, and should be construed complementarily to the preferred embodiment.

Figure 7:
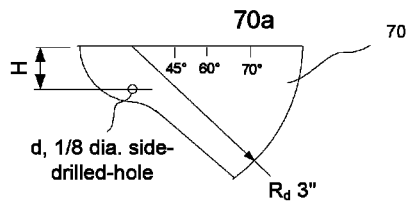
FIG. 7 illustrates the geometric parameters associated with a DSC block used in the calculation of true refraction angles.

The first alternative embodiment involves the usage of a DSC block 70, as shown in FIG. 7, instead of IIW block for phased-array refraction angle verification.

Referring to FIG. 7, alternatively the DSC block is used for the refraction angle verification. The definition and usage of the DSC block is provided by "Qualification and Calibration of UT Units with Other Approved Reference Blocks" from *AWS* D1.1/D1.1M:2006, *Structural Welding Code* (later as "AWS DSC Block"), herein incorporated by reference. The calibration procedure described in the above reference is a manual process for single element ultrasonic devices (UT).

The instrument built-in procedure for phased array (PA) refraction angle verification using DSC block 70 according to the present disclosure is described below.

Figure 8:
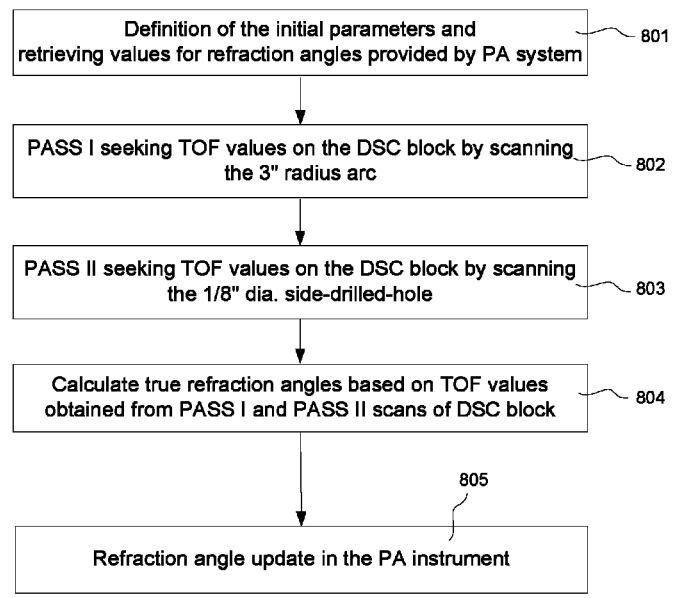
FIG. 8 is a flow-chart depicting the method and process according to an alternative embodiment of using DSC block to perform refraction angle verification.

According to FIG. 8, the refraction angle verification with DSC block can be achieved with a process that includes steps 801 through 805. Steps 801 to 803 require the user's interactions and steps 804 through 805 are executed automatically by refraction verification module 2 of FIG. 1.

In step 801, the user inputs the parameters of the DSC block (see FIG. 7 for the DSC block geometric parameter definitions) as follows.

$R_d$, (normally 3"), the largest radius of DSC block 70.
d, (normally ⅛"), the diameter of the side-drilled hole.
H, (normally 0.75"), the depth of the center of the ⅛" side-drilled hole, measured from surface 70a of the DSC block.
$V_d$, the wave velocity of the DSC block that can be obtained similarly with the Distance Calibration procedure described in reference AWS DSC Block.

The "range of refraction angle" for verification. (For a sectorial scan, the range of refraction angles can be part or the full range of the refraction angles of a specific probe/wedge unit. For a linear scan, the range of refraction angle is the selected range of the angles). The angles to check should be within the angle range of DSC blocks.

Continuing with FIG. 8, in step 802, the user scans (making Pass I) the PA probe and wedge unit 8 through the center of the arcuate surface of radius $R_d$. At the same time, similar to what is described in step 202, the angle verification module 2 instructs the system 1 to record, for each focal law, the full TOF associated with the maximum amplitude response measured, i.e., $t_{d1i}$ (i=1, 2, . . . to the maximum focal law number).

In Step 803, the user scans (making Pass II) PA probe and wedge unit 8 the 1/8" diameter side-drilled hole in DSC block 70. At the same time, refraction angle verification module 2 instructs PA system 1 to record, for each focal law, the full TOF associated with the maximum amplitude response measured, i.e., $t_{d2i}$ (i=1, 2, . . . to the maximum law number). Herein "d" in $t_{d1i}$ and $t_{d2i}$ denotes the usage of DSC block, differentiating from the IIW block. Also, "1" denotes Pass I in step 802 and "2" denotes Pass II in step 803.

In step 804, refraction angle verification module 2 calculates the true refraction angles of the focal laws that were applied during Pass I and Pass II as follows.

$T_{d1}$, which is the full TOF from the center of the radius R to the arcuate surface and can be calculated as:

$$T_{d,const} = 2 \times R_d / V_d, \quad \text{Eq. 6}$$

It should be noted that $T_{d,const}$ is a constant value for all angle beams.

Full delay in wedge for each law:

$$T_{d0i} = t_{d1i} - T_{d,const}, \quad \text{Eq. 7}$$

where,
i=1, 2, . . . to the maximum law number.

TOF from the beam exit point to the 1/8" dia. side-drilled hole surface for each law:

$$T_{d2i} = t_{d2i} - T_{d0i}, \quad \text{Eq. 8}$$

where,
i=1, 2, . . . to the maximum law number.

The sound path from the beam exit point to the 1/8" dia. side-drilled hole surface for each law:

$$L_{d2i} T_{d2i} \times V_d / 2, \quad \text{Eq. 9}$$

where,
i=1, 2, . . . to the maximum law number.

Finally, the beam refracting angle in the DSC block for each law:

$$A_{di} = \arccos\left(\frac{H}{d/2 + L_{d2i}}\right), \quad \text{Eq. 10}$$

where,
i=1, 2, . . . to the maximum law number.

$A_{di}$ is the actual refraction angle of each angle beam corresponding to each focal law applied.

In step 805, the PA instrument's setup is updated with the actual beam refraction angles $A_{di}$ and the wedge delays $T_{d0i}$.

Figure 9:
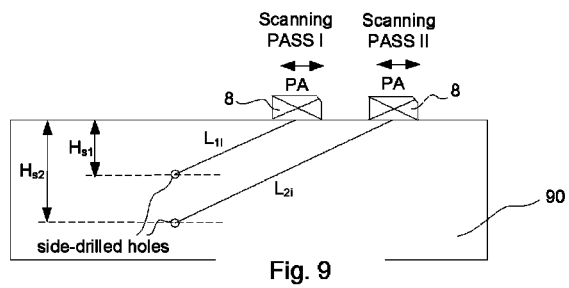
FIG. 9 illustrates the geometric parameters associated with a SDH block used in the calculation of true refraction angles.

The second alternative embodiment involves the usage of a block with at least two side-drilled holes (SDH) such as a Nayships block instead of IIW block for phased-array refraction angle verification. A custom SDH block 90 is shown in FIG. 9. Custom SDH block 90 has two side-drilled holes at different depths and can be used in the same manner as a standard Nayships block. These blocks and any other blocks with at least two side-drilled holes at different depths in the block are referred to herein as SDH blocks.

The instrument built-in procedure for phased array (PA) refraction angle verification using custom SDH block 90 or alternatively a Nayships block according to the present disclosure is described below.

Figure 10:
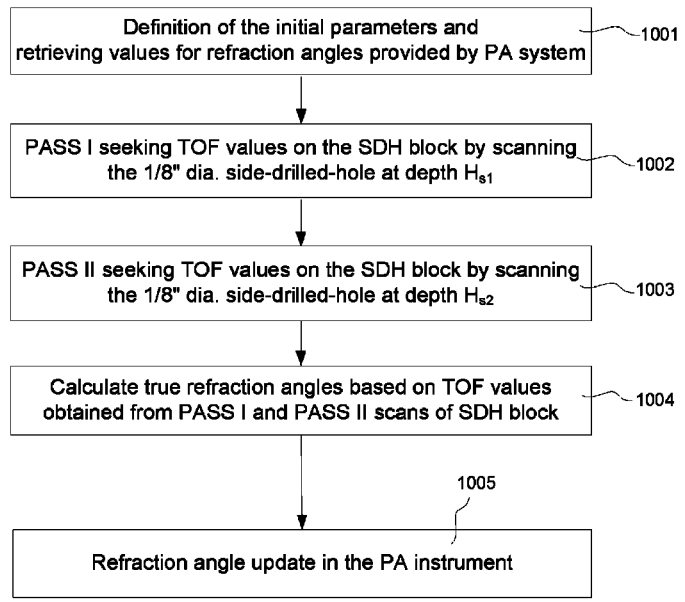
FIG. 10 is a flow-chart depicting the method and process according to an alternative embodiment of using a SDH block to perform refraction angle verification.

According to FIG. 10, the refraction angle verification with a SDH block can be achieved with a process that includes steps 1001 through 1005. Steps 1001 to 1003 require user's interactions and steps 1004 through 1005 are executed automatically by refraction verification module 2 of FIG. 1.

In step 1001, the user inputs the parameters of the SDH block as follows.

$H_{s1}$, the depth of the shallowest side-drilled hole to be used for verifying the steering angles.

$H_{s2}$, the depth of the deepest side-drilled hole to be used for verifying the steering angles.

$V_s$, the wave velocity of the SDH block. The refraction angle check procedure of the present disclosure requires beforehand knowledge of the sound wave velocity in the SDH block.

The "range of refraction angle" for verification. (For a sectorial scan, the range of refraction angles can be part or the full range of the refraction angles of a specific probe/wedge unit. For a linear scan, the range of refraction angle is the selected range of the angles). The angles for verification should be within the angle range of the SDH block.

Continuing with FIG. 10, in step 1002, the user scans (making Pass I) the 1/8" diameter side-drilled hole at depth $H_{s1}$ in SDH block 90 using PA probe and wedge unit 8. At the same time, similar to what is described in step 202, the angle verification module 2 instructs the system 1 to record, for each focal law, the full TOF associated with the maximum amplitude response measured, i.e., $t_{s1i}$ (i=1, 2, . . . to the maximum focal law number).

In Step 1003, the user now scans (making Pass II) the 1/8" diameter side-drilled hole at depth $H_{s2}$ in SDH block 90 using PA probe and wedge unit 8. At the same time, refraction angle verification module 2 instructs PA system 1 to record, for each focal law, the full TOF associated with the maximum amplitude response measured, i.e., $t_{s2i}$ (i=1, 2, . . . to the maximum law number). Herein "s" in $t_{s1i}$ and $t_{s2i}$ denotes the usage of a SDH block, differentiating from the IIW block. Also, "1" denotes Pass I in step 1002 and "2" denotes Pass II in step 1003.

In step 1004, refraction angle verification module 2 calculates the true refraction angles of the focal laws that were applied during Pass I and Pass II as follows.

The time difference between $t_{s1i}$ and $t_{s2i}$ for each law is simply due to the sound path difference between the two side-drilled holes and leads to a beam refraction angle:

$$A_{si} = \arccos\left(\frac{H_{s2} - H_{s1}}{V_s \times (t_{s2i} - t_{s1i})}\right), \quad \text{Eq. 11}$$

where,
i=1, 2, . . . to the maximum law number.

$A_{si}$ is the actual refraction angle of each angle beam corresponding to each focal law applied.

In step 1005, the PA instrument's setup is updated with the actual beam refraction angles $A_{si}$.

It should be appreciated by those skilled in the art that the use of two separate gates for simultaneously acquiring within one scan pass $t_{s1i}$ and $t_{s2i}$ would lead this embodiment to using a single pass thereby combining steps 1002 and 1003 into a single operation by the user.

Optionally with this embodiment, wedge delay values for each focal law ($T_{s0i}$) can be calculated and provided by the angle verification module 2 according to the following formula:

$$T_{s0i} = t_{sji} - \frac{(H_{sj} - (\cos A_{si} \times d/2))}{V_s \times \cos A_{si}}, \quad \text{Eq. 12}$$

where, d is the diameter of the side-drilled hole at a depth of $H_j$ below the surface of the SDH block.

i=1, 2, . . . to the maximum law number.

j=1 or 2 and corresponds to either first or second side-drilled hole used in the calibration.

It is worth noting that any calibration block that has fixed and known ultrasonic and relevant geometric characteristics can be used for the purpose of PA beam angle verification using the herein disclosed method.

Although the present invention has been described in relation to particular exemplary embodiments thereof, many other variations and modifications and other uses will become apparent to those skilled in the art. It is preferred, therefore, that the present invention not be limited by the specific disclosure.

What is claimed is:

1. An ultrasonic phased array non-destructive inspection system, comprising, an ultrasonic phased array inspection probe, an ultrasonic phased array inspection unit configured to control the ultrasonic phased array probe to emit ultrasonic signals in a form of a plurality of angle beams into an industrially standard ultrasonic calibration block, to receive a set of corresponding echo signals reflected from the industrially standard ultrasonic calibration block and to provide time-of-flight (TOF) values corresponding to each of said angle beams, wherein the industrially standard ultrasonic calibration block has fixed and known geometric and physical characteristics, and a refraction angle verification unit configured to be in communication with the ultrasonic phased array inspection unit, and to use a predetermined calibration procedure, to provide a true angle for each of the angle beams based on the characteristics of the industrially standard ultrasonic calibration block and the TOF values;

wherein the standard block includes a first reflector and a second reflector and a first scanning side and a second scanning side;

and, wherein during the predetermine calibration procedure, the refraction angle verification unit is configured to perform a procedure including, a) instructing the phased array inspection unit and the probe to emit the angle beams with a first set of predetermined system-assumed angles within a first angle range and to receive the corresponding echo signals, targeting the first reflector, b) retrieving the TOF values as $t_{1i}$ corresponding to the angle beams from the inspection unit regarding the first reflector with "i" denoting each of the first set of system-assumed angles, c) instructing the phased array inspection unit and the probe to emit the angle beams with a second set of predetermined system-assumed angles within a second angle range and to receive the corresponding echo signals, targeting the second reflector, d) retrieving the TOF values as $t_{2i}$ corresponding to the angle beams from the inspection unit regarding the second reflector with "i" denoting each of the second set of system-assumed angles, e) calculating the true angles of the corresponding angle beams based on the TOF values and the geometric and physical characteristics of the calibration block according to a set of predetermined angle determination formulae, and f) replacing the system-assumed angles with the true angles of the angle beams.

2. The system of claim 1, wherein the known geometric and physical characteristics of the industrially standard ultrasonic calibration block include, a) R, an arcuate surface radius of the first reflector;

b) r, a radius of the second reflector;

c) $H_1$, a depth of the center of the first reflector measured from the first scanning side of the industrially standard ultrasonic calibration block, d) $H_2$, a depth of the center of the second reflector measured from the second scanning side of the industrially standard ultrasonic calibration block, e) V, a wave velocity of the industrially standard ultrasonic calibration block.

3. The system of claim 2, wherein the set of predetermined angle determination formulae include, $$T_1 2 \times R/V,$$

$$T_{0i} = t_{1i} - T_1,$$

$$T_{0i} = t_{1i} - T_1,$$

$$T_{2i} = t_{2i} - T_{0i},$$

$$L_{2i} = T_{2i} \times V/2, \text{ where:}$$

true refraction angles within the first angle and $$\text{range} = \arccos\left(\frac{H_1}{r + L_{2i}}\right),$$

true refraction angles within the second angle $$\text{range} = \arccos\left(\frac{H_2}{r + L_{2i}}\right),$$

in the term $T_{1i}$, i stands for i number of focal law and the 1 numeric represents the first scan-pass; and in the term $T_{2i}$ represents the focal law number and the 2 numeric represents the second scan.

4. The system in claim 1, wherein the angle verification unit comprises an executable software process loaded onto a digital data processor of the phased array inspection unit.

5. The system in claim 1, wherein the angle verification unit comprises an executable software process loaded onto a digital data processor in communication with the phased array inspection unit.

6. The system of claim 1, wherein the industrially standard ultrasonic calibration block is an HIV Block.

7. The system of claim 1, wherein the industrially standard ultrasonic calibration block is a DSC Block.

8. The system of claim 1, wherein the industrially standard ultrasonic calibration block is a side-drilled-hole (SDH) block.

9. A method of performing calibration on an ultrasonic phased array non-destructive inspection system, wherein the inspection system includes an inspection probe, an ultrasonic phased array inspection unit configured to control the inspection probe to emit ultrasonic signals in a form of plurality of angle beams into an industrially standard ultrasonic calibration block, to receive a set of corresponding echo signals reflected from the industrially standard ultrasonic calibration block and to provide time-of-flight (TOF) values corresponding to each of the angle beams and a refraction angle verification unit configured to be in communication with the ultrasonic phased array inspection unit, wherein the industrially standard ultrasonic calibration block has fixed and known geometric and physical characteristics, the method comprising steps of:

a) instructing the ultrasonic phased array inspection unit and the inspection probe to emit the angle beams with a first set of predetermined system-assumed angles within a first angle range and to receive the corresponding echo signals, targeting a first reflector of the industrially standard ultrasonic calibration block, b) retrieving the TOF values as $t_{1i}$ corresponding to the angle beams from the inspection unit regarding the first reflector, with i denoting each of the first set of system-assumed angles, c) instructing the phased array inspection unit and the probe to emit the angle beams with a second set of predetermined system-assumed angles within a second angle range and to receive the corresponding echo signals, targeting a second reflector of the industrially standard ultrasonic calibration block, d) retrieving the TOF values as $t_{2i}$ corresponding to the angle beams from the inspection unit regarding the second reflector, with i denoting each of the second set of system-assumed angles, e) calculating true angles of the corresponding angle beams based on the TOF values and the geometric and physical characteristics of the calibration block according to a set of predetermined angle determination formulae, and f) replacing the system-assumed angles with the true angles of the angle beams.

10. The method of claim 9, wherein the geometric and physical characteristics of the block include:

f) R, an arcuate surface radius of the first reflector;

g) r, a radius of the second reflector;

h) $H_1$, a depth of the center of the first reflector measured from the first scanning side of the block, i) $H_2$, a depth of the center of the second reflector measured from the second scanning side of the block, and j) V, a wave velocity of the block.

11. The method of claim 10, wherein the angle determination formulae include:

$$T_1 = 2 \times R/V,$$

$$T_{0i} = t_{1i} - T_1,$$

$$T_{2i} = t_{2i} - T_{0i},$$

$$L_{2i} = T_{2i} \times V/2,$$

wherein the true refraction angles within the first angle and $$\text{range} = \arccos\left(\frac{H_1}{r + L_{2i}}\right),$$

the true refraction angles within the second angle $$\text{range} = \arccos\left(\frac{H_2}{r + L_{2i}}\right),$$

in the term $T_{1i}$, i stands for i number of focal law and the 1 numeric represents the first scan-pass; and in the term $T_{2i}$, i represents the focal law and the 2 numeric represents the second scan.

12. The method in claim 9, wherein the refraction angle verification unit comprises an executable software process loaded onto a digital data processor of the ultrasonic phased array inspection unit.

13. The method in claim 9, wherein the refraction angle verification unit comprises an executable software process loaded onto a digital data processor in communication with the ultrasonic phased array inspection unit.

14. The method of claim 9, wherein the industrially standard ultrasonic calibration block is a HIV Block.

15. The method of claim 9, wherein the industrially standard ultrasonic calibration block is a DSC Block.

16. The method of claim 9, wherein the industrially standard ultrasonic calibration block is a side-drilled-hole (SDH) block.

* * * * *